US012728262B2

(12) United States Patent
Kamenz et al.

(10) Patent No.: US 12,728,262 B2
(45) Date of Patent: Sep. 8, 2026

(54) MEDICAL ELECTRODE DEVICE COMPRISING AT LEAST ONE CONTACT ELEMENT AND METHOD FOR FABRICATING SAME

(71) Applicant: BIOTRONIK SE & Co. KG, Berlin (DE)

(72) Inventors: Toni Kamenz, Eggersdorf (DE); Carsten Fruendt, Berlin (DE)

(73) Assignee: BIOTRONIK SE & Co. KG, Berlin (DE)

( * ) Notice: Subject to any disclaimer, the term of this patent is extended or adjusted under 35 U.S.C. 154(b) by 213 days.

(21) Appl. No.: 18/839,595

(22) PCT Filed: Feb. 20, 2023

(86) PCT No.: PCT/EP2023/054147
§ 371 (c)(1),
(2) Date: Aug. 19, 2024

(87) PCT Pub. No.: WO2023/165829
PCT Pub. Date: Sep. 7, 2023

(65) Prior Publication Data

US 2025/0170390 A1 May 29, 2025

(30) Foreign Application Priority Data

Mar. 1, 2022 (EP) .................................... 22159427

(51) Int. Cl.
*A61N 1/05* (2006.01)

(52) U.S. Cl.
CPC ................................ *A61N 1/0553* (2013.01)

(58) Field of Classification Search
None
See application file for complete search history.

(56) References Cited

U.S. PATENT DOCUMENTS 3,654,933 A * 4/1972 Hagfors .................. A61N 1/05 607/118
5,295,872 A * 3/1994 Christensson ......... A61N 1/048 439/822

(Continued)

FOREIGN PATENT DOCUMENTS

EP 2108398 A1 10/2009

OTHER PUBLICATIONS

Extended European Search Report mailed Sep. 14, 2022, by the European Patent Office for corresponding Application No. EP22159427. 8. (8 pages).

(Continued)

*Primary Examiner* — Michael T. Holtzclaw
(74) *Attorney, Agent, or Firm* — Buchanan Ingersoll & Rooney PC

(57) ABSTRACT

A medical electrode device for implantation into a patient includes:

a carrier element, a contact element on the carrier element and comprising a contact body including a contact surface for contacting tissue, and an electrical supply line having an end portion connected to the contact element. The contact element comprises first and second fastening flaps arranged at a distance with respect to each other. The electrical supply line connected to the contact element at the first and second flaps. Each flap extends from a circumference of the contact body with a first end integral with the contact body and a second end free. Each flap comprises a bent portion proximal to the circumference of the contact body and a straight portion distal to such circumference. Each flap connected to the supply line with a lateral contact surface extending along a side edge of the straight portion of the respective flap.

15 Claims, 6 Drawing Sheets

(56) References Cited

U.S. PATENT DOCUMENTS

| | | | | |
|---|---|---|---|---|
| 5,431,166 | A * | 7/1995 | Macur | A61N 1/048 607/152 |
| 6,052,608 | A | 4/2000 | Young et al. | |
| 6,895,283 | B2 | 5/2005 | Erickson et al. | |
| 9,561,363 | B2 | 2/2017 | Skubitz et al. | |
| 2005/0154435 | A1 | 7/2005 | Stern et al. | |
| 2008/0046050 | A1 | 2/2008 | Skubitz et al. | |
| 2012/0135624 | A1 * | 5/2012 | Putz | H01R 4/5008 439/668 |
| 2014/0172057 | A1 | 6/2014 | Orinski | |
| 2018/0369575 | A1 | 12/2018 | Dubuclet et al. | |
| 2021/0052885 | A1 * | 2/2021 | Kaula | A61N 1/0558 |
| 2021/0138237 | A1 | 5/2021 | Willenberg et al. | |

OTHER PUBLICATIONS

International Search Report (PCT/ISA/210) and Written Opinion (PCT/ISA/237) mailed Apr. 6, 2023, by the European Patent Office as the International Searching Authority for International Application No. PCT/EP2023/054147. (8 pages).

* cited by examiner

MEDICAL ELECTRODE DEVICE COMPRISING AT LEAST ONE CONTACT ELEMENT AND METHOD FOR FABRICATING SAME

CROSS-REFERENCE TO RELATED APPLICATIONS

This application is the United States National Phase under 35 U.S.C. § 371 of PCT International Patent Application No. PCT/EP2023/054147, filed on Feb. 20, 2023, which claims the benefit of European Patent Application No. 22159427.8, filed on Mar. 1, 2022, the disclosures of which are hereby incorporated by reference herein in their entireties.

TECHNICAL FIELD

The present invention relates to a medical electrode device for implantation into a patient and to a method for fabricating a medical electrode device.

BACKGROUND

A medical electrode device may, for example, serve for neuro-stimulation, i.e., for stimulating nerves within a body of a patient by applying electric voltages or currents. For this, the medical electrode device may be implanted into the patient, for example, in the region of the spinal cord, for example, into the epidural space near the spinal cord of the spinal column of a patient.

An electrode device of the kind concerned herein however may also be used for emitting stimulation signals or receiving sense signals at other locations within a patient, for example, within the brain or in cardiac applications.

An electrode device of the kind concerned herein comprises a carrier element being formed from an electrically insulating material, at least one contact element arranged at the carrier element and comprising a contact surface for coupling to tissue in an implanted state of the medical electrode device, and at least one electrical supply line connected to the at least one contact element.

The medical electrode device may be configured as a so-called paddle electrode. In this case, the carrier element has a flattened, paddle-like shape carrying, e.g., an arrangement of multiple evenly or unevenly distributed contact elements on its surface for emission of electrical signals into and/or reception of electrical signals from surrounding tissue of the patient.

U.S. Pat. Nos. 6,052,608, 6,895,283, 9,561,363, European Publication No. 2 108 398 A1, U.S. Publication No. 2008/0046050 A1 and U.S. Publication No. 2014/0172057 A1 disclose various conventional medical electrode devices.

In a prior European Patent Application with the application number EP21212321.0, the present applicant disclosed a medical electrode device having some features in common with the medical electrode device described herein. Some characteristics of the medical electrode device described in this prior application may be applied in a same or similar manner to the medical electrode device described herein. Accordingly, the content of this prior application shall be incorporated herein in its entirety by reference.

The present disclosure is directed toward overcoming one or more of the above-mentioned problems, though not necessarily limited to embodiments that do.

SUMMARY

It is an object of the instant invention to provide a medical electrode device and a method for fabricating a medical electrode device allowing for an easy, reliable and/or cost-efficient fabrication as well as an improved mechanical stability of one or multiple contact elements on a carrier element.

At least this object may be achieved by the subject matter of the independent claims. Advantageous embodiments are disclosed in the dependent claims and the following specification as well as in the associated figures.

According to a first aspect of the present invention, a medical electrode device for implantation into a patient is proposed. The electrode device comprises a carrier element, at least one contact element and at least one electrical supply line. The carrier element is formed from an electrically insulating material. The contact element is arranged at the carrier element and comprises a contact body including a contact surface for contacting tissue of the patient when the medical electrode device is in an implanted state. The electrical supply line comprises an end portion being electrically connected to the contact element. The contact element comprises at least one first fastening flap and at least one second fastening flap. The first fastening flap and the second fastening flap are arranged at a distance with respect to each other along a length direction. The electrical supply line is connected to the contact element at the first fastening flap and the second fastening flap such that the electrical supply line is arranged at a distance with respect to the contact surface along a height direction oriented perpendicularly to the length direction. Each of the first and second flaps extends from a circumference of the contact body with a first end of each flap being integral with the contact body and a second end of each flap being free. Each of the first and second flaps comprises a bent portion proximal to the circumference of the contact body and a straight portion distal to the circumference of the contact body. Furthermore, each of the first and second flaps is connected to the electrical supply line with a lateral contact surface extending along a side edge of the straight portion of the respective flap.

According to a second aspect of the present invention, a method for fabricating a medical electrode device is described. The method comprises providing a carrier element, at least one contact element and at least one electrical supply line, wherein these components generally may have the characteristics defined for embodiments of the above first aspect of the present invention. The method comprises arranging the contact element at least partially in the electrically insulating material of the carrier element such that the contact element comprises a contact surface for coupling to tissue of the patient in an implanted state of the medical electrode device and, preferably in a subsequent method step, connecting each of the first and second flaps to the electrical supply line with a lateral contact surface extending along a side edge of the straight portion of the respective flap.

Ideas underlying embodiments of the present invention may be interpreted as being based, inter alia, on the following observations and recognitions.

Briefly summarised in a non-limiting manner, embodiments of the present invention relate to a medical electrode device such as a paddle electrode for neurostimulation, in which one or plural contact elements are accommodated within a carrier element of electrically insulating material and wherein each contact element is reliably electrically connected to an electrical supply line. The contact element comprises flaps extending from a circumferential rim of a contact body. Such flaps are bended in a manner such as to comprise a bent portion and a straight portion. The bent portion is arranged at a first end of the flap where the flap integrally adjoins the rim of the contact body, whereas the straight portion is arranged further distally at a second end of the flap forming a free end. Specifically, the flaps are bent and shaped such that at least the straight portion extends in a direction parallel to a longitudinal direction of an end portion of the electrical supply line connected to the contact element. Therein, each flap is connected to the respective electrical supply line along a lateral contact surface. This lateral contact surface extends along a side edge of the straight portion of the respective flap.

While, in conventional approaches, the electrical supply line is generally connected to the contact body only along short areas corresponding, for example, to a sheet thickness of a metal sheet forming the contact body, in the approach described herein, the electrical supply line is connected to the contact body along the side edge of the flap's straight portion. This side edge generally is substantially longer than the sheet thickness of the flap. Accordingly, due to such long lateral contact surface between the flap and the electrical supply line, the contact element and the electrical supply line may be precisely aligned with respect to each other and may be reliably connected with each other. Thereby, an entire fabrication process as well as the fabricated electrode device may be improved with regards to reliability, cost efficiency and/or automation.

In the following, possible characteristics and advantages of embodiments of the present invention will be described in more detail.

The medical electrode device described herein is configured for being implanted into a patient. Accordingly, its dimensions are adapted for fitting into an available volume within the body of the patient. For example, the electrode device may have an elongate shape with a length of several centimetres (e.g., 2-20 cm), a substantially smaller with (e.g., 0.5-4 cm) and an even smaller thickness (e.g., 0.2-1 cm). Furthermore, at least those components and areas of the electrode device being in contact with the patient's tissue are made with biocompatible materials.

The electrode device comprises a carrier element, one or, preferably, a plurality of contact elements and one or, preferably, a plurality of electrically supply lines connected to the contact element(s).

The carrier element consists of or comprises electrically insulating material. For example, silicone or polymeric materials may be used for the carrier element. The carrier element and/or its material may be elastically deformable. The carrier element may have an elongate shape.

The contact element consists of or comprises an electrically conductive material. For example, metals, preferably biocompatible metal such as titanium or metal alloys such as platinum iridium alloys may be used for the contact element. The contact element may be rigid or may at least be less electrically deformable than the carrier element. The contact element may have an arbitrary shape. For example, the contact body of the contact element may have a cuboid, i.e., substantially box-shaped geometry, possibly with a rounded edges. The dimensions of the contact element may be small with a length and width being, for example, smaller than 10 mm, smaller than 5 mm or even smaller than 3 mm. A sheet thickness of material forming the contact element may be thin, e.g., in a range of 0.1-0.5 mm. Having such small dimensions and sheet thickness, reliably fixing the contact element to the electrical supply line is generally no simple task.

The electrical supply line consists of or comprises an electrically conductive material. For example, metals, preferably electrically highly conductive metal such as copper, aluminium, etc. may be used for the supply line. The supply line may be supple and/or easily bendable. For example, the supply line may be more deformable than the carrier element. In that case, the supply line may be easily deformed into a required shape upon being installed in the carrier element. The supply line may be provided, e.g., with a multiplicity of strands, cords or litzes. Alternatively, the supply line may be relatively rigid and may, for example, be less easily deformable than the carrier element. In that case, the supply line may be pre-formed in a predefined shape before being installed in the carrier element.

The carrier element may have one or more recesses, cavities or the like in which one or more contact elements may be accommodated. Particularly, the recesses, cavities or the like may be configured such that the contact elements may be arranged therein such that at least a portion of the contact body of the contact element is exposed from the carrier element and therefore forms the contact surface via which the contact element may mechanically and/or electrically contact adjacent tissue of the patient upon being implanted in the patient's body.

Upon fabricating the electrode device, the contact element may be arranged at or in the carrier element. Preceding, simultaneous or following to such arranging of the contact element, the corresponding electrical supply line may be arranged at or in the carrier element. Therein, the supply line typically extends from an end of the carrier element to a position at which the contact element is arranged. Subsequently, an end portion of the supply line is electrically connected to the contact element.

For simplifying a procedure of contacting the contact element by the supply line upon fabricating the entire electrode device, the contact element comprises first and second fastening flaps. Such flaps may also be referred to as tabs or lugs. An end portion of the supply line may then be attached to at least two of such flaps. Preferably, the supply line is attached using techniques forming a positive substance jointing, such as welding, soldering, etc.

Therein, a first fastening flap and a second fastening flap are arranged at the contact element at locations being spaced from each other along a length direction. Such length direction generally corresponds to a longitudinal direction of the supply line or of the end portion of the supply line to be connected with the contact element. Accordingly, the supply line may be attached to the first fastening flap at a further proximal position at the contact element and may be attached to the second fastening flap at a further distal position at the contact element.

Furthermore, the first and second fastening flaps and the contact element are arranged and configured such that, upon the electrical supply line being attached to the flaps, the supply line is arranged such as to be spaced apart from the contact surface of the contact element in a height direction oriented perpendicular to the length direction.

Each of the flaps may have an elongate shape. Therein, a length of the flap may be longer than its width. A length direction of the flap may be parallel to the length direction of the contact element and/or of the entire electrode device.

Each flap protrudes from the contact body of the contact element at a location positioned at a circumference of the contact body. Therein, a first end of the flap is integral with the contact body. Preferably, the contact body and the flap are made from a common metal sheet. Therein, the flaps are arranged at a circumferential rim of the metal sheet. A second end of the flap is free, i.e., may protrude from the metal sheet also forming the contact body.

Compared to prior art approaches, particularly compared to the approach described in the applicant's own prior art approach as indicated in the above introductory portion, an arrangement and/or orientation of the first and second flaps with regards to the rest of the contact element substantially differs in the approach described herein.

Particularly, in the cited prior art approach, the flaps are generally straight or a planar along their entire extension and a longitudinal direction of the flaps is perpendicular to the length direction of the contact element. Accordingly, the flap extends substantially perpendicular to the electrical supply line. Thus, the supply line may be electrically and mechanically connected to the flap only along a very small surface corresponding to a material thickness of the flap, i.e., a material thickness of the metal sheet forming the flap or, in other words, along a side edge of the straight portion of the respective flap.

In contrast hereto, in the approach described herein, the flaps comprise a bent portion. In other words, the flap is not completely straight or planar along its entire extension but comprises a portion which is significantly bent. Therein, the bent portion is arranged proximally at the flap, i.e., may adjoin the circumference of the contact body, whereas the straight portion is arranged distally at the flap and generally forms the second, free end of the flap. A curvature radius of the flap in the bent portion is substantially smaller than in the straight portion. Particularly, the curvature radius in the bent portion is generally smaller than the length of the flap and may, for example, be smaller than 1 mm or even smaller than 0.3 mm. In contrast hereto, the straight portion may have no curvature, i.e., may be planar, or may have a very large curvature radius being longer than the length of the flap, e.g., longer than 10 mm. Having such combination of a bent portion and a straight portion, the flap may be arranged with its straight portion being substantially parallel to the length direction of the contact element, i.e., being parallel to the longitudinal direction of the electrical supply line.

Accordingly, a side edge of the straight portion of each of the flaps may extend generally parallel to the electrical supply line. Thus, the supply line may abut against the side edge of the respective flap along a substantial length. As a result, each of the flaps may be electrically and/or mechanically connected to the electrical supply line such that a lateral contact surface between the flap and the supply line extends along the side edge of the straight portion of the flap. Due to such contact surface having a substantial length possibly corresponding to the longitudinal length of the straight portion of the flap, a reliable and/or loadable connection may be established between the supply line, on the one hand, and the first and second flaps at the contact element, on the other hand.

According to an embodiment, each of the first and second flap comprises a lateral rim extending along a side edge of the straight portion of the respective flap, wherein a circumferential surface of an end portion of the electrical supply line is arranged at the lateral rim, and particularly joined with. Advantageously, the side edge, or more specifically the lateral rim serves as surface stop or guide for the electrical supply line, which facilitates a proper arrangement and attachment of the electrical supply line to the respective contact element.

According to an embodiment, the first flap extends from a first end edge of the contact body and the second flap extends from a second end edge opposite to the first end edge of the contact body. Furthermore, each of the first and second flaps is directed with its second end towards a center of the contact body.

In other words, the first and second flaps project from respective opposite edges forming a circumference of the contact body. For example, the first flap extends from a proximal edge of the contact body whereas the second flap extends from a distal edge of the contact body, when seen in the length direction of the contact element. Both, the first and second flaps are bent such that their respective second free ends are directed towards a center of the contact body. Such center may correspond to a geometric middle line extending in a direction rectangular to the length direction and extending through the middle between the first and second flaps. Accordingly, the second ends of the first and second flaps face each other. Furthermore, both, the first and second flaps do not protrude in an outward direction with regard to the contact body but are directed in an inward direction towards the center of the contact body and therefore at least partially overlap the contact body.

According to an embodiment, a lateral rim of the respective flap extending along a side edge of the straight portion of the flap is welded, preferably laser welded, to a circumferential surface of an end portion of the electrical supply line.

Welding the lateral rim of a flap to a surface of the supply line generally provides for a very reliable positive substance jointing between both components. Contrary to, for example, soldering techniques, welding techniques generally do not require providing any additional substances for generating the positive substance jointing. Accordingly, welding techniques may be beneficially applied in an industrial fabrication line.

Particularly, laser welding may be applied for reliably and precisely welding small and/or thin components and may therefore be advantageous for welding the thin flaps of the contact element to the electrical supply line of small diameter. Therein, a laser beam is generally directed towards an interface between the lateral rim of the flap and the adjacent end portion of the supply line.

Particularly, it has been found that, in the approach proposed herein, arranging the straight portion of the flap such as to be parallel to the supply line and, preferably, such as to superimpose other portions of the contact body may provide the positive effect that, even upon undesired cases in which the welding laser beam is not perfectly aligned with the flap's lateral rim, the laser beam will not impact onto material of the carrier element but, instead, will reach other portions of the contact element. While the laser beam irradiating material of the carrier element would probably damage such material, the laser beam reaching the typically metallic material of the contact element generally does not substantially harm this material.

Accordingly, even upon temporary misalignment of the welding laser beam, the specific configuration and arrangement of the first and second flaps in the approach proposed herein enables preventing any damages to the electrode device due to the flaps and the adjacent other portions of the contact element forming a kind of "laser beam trap" preventing the laser beam from hitting more sensitive portions of the electrode device.

According to an embodiment, the contact body comprises a first flange extending along a first rim portion of the contact body and a second flange extending along a second rim portion of the contact body opposite to the first rim portion. Therein, the first flap extends from the first flange and the second flap extends from the second flange.

The first and second flanges may be straight or planar portions of the contact element. Such flanges may extend at opposite rim portions of the contact body. The flanges may be arranged at a distance with respect to the contact surface of the contact element along the height direction. The first and second flanges may extend in parallel to the contact surface of the contact element. The first and second flanges may extend in a common plane.

Upon fabricating the electrode device, the supply line may be disposed on the first and second flanges and may thereby be aligned in the height direction with respect to the contact element. As the flanges generally have a large abutment surface, the supply line may be disposed on the flanges along a significant area and may therefore be reliably supported by the flanges. Particularly, the abutment surface of each of the flanges may be substantially larger than a cross-sectional surface of sheet material forming the contact element.

According to a further specified embodiment, the straight portions of each of the first and second flaps extend, with a tolerance of ±30°, preferably with a tolerance of ±20° or ±10°, in parallel to the flange from which the respective flap extends.

In other words, while the bent portion of the flaps may generally directly adjoin the flange of the contact element, the straight portion of the flaps may be arranged such as to extend substantially parallel to the flange. Therein, the straight portion of the flap covers or overlaps at least a portion of the flange.

According to another further specified embodiment, the electrical supply line abuts with a portion of its lateral surface to each of the first and second flanges.

Thus, the flange may form an abutment surface for the supply line in the height direction. Furthermore, the flap may form an abutment surface in a lateral direction perpendicular to such height direction. Accordingly, by disposing the supply line with its lateral surface abutting against both, the abutment surface formed by the flange and the abutment surface formed by the lateral rim of the flap, the supply line may be precisely positioned and aligned with respect to the contact element and may then be reliably connected to the flap and thereby be fixed to the contact element.

According to an embodiment, the bent portion of the flap is bent such that the straight portion of the flap directly abuts to a portion of the contact body.

In other words, the bent portion may be provided with such a small curvature radius such that the adjoining straight portion of the flap is in direct mechanical contact with an adjacent portion of the contact body. The curvature radius of the bent portion may, e.g., be 0 or may be close to 0. For example, if the flap extends from a flange at the contact element, the straight portion of the flap may directly abut to the flange. Thereby, effectively, a larger material thickness is formed in a region where the straight portion of the flap overlaps the flange. In fact, the material thickness may be doubled relative to a sheet thickness of a metal sheet forming the contact element. Such larger material thickness may be beneficial, e.g., upon welding the flap's rim to the supply line.

According to an alternative embodiment, the bent portion of the flap is bent such that the straight portion of the flap is spaced from a portion of the contact body via an intermediate gap.

Expressed differently, the bent portion may be provided with a curvature radius being substantially larger than 0. Fr example, the curvature radius may be similar or larger than a sheet thickness of a metal sheet forming the contact element. Accordingly, the adjoining straight portion of the flap is not in direct mechanical contact but is parallel and spaced apart from the adjacent portion of the contact body. For example, a gap between the straight portion of the flap and the adjacent portion of the contact body may be larger than 0.01 mm, preferably larger than 0.5 mm or larger than 0.1 mm. Such gap may, inter-alia, provide for a thermal isolation between the flap and the adjacent portion of the contact body. Accordingly, it may be, for example, prevented that heat generated upon welding the flap to the supply line may be excessively transmitted to other portions of the contact body, these portions being, for example, in thermal contact with temperature sensitive material, e.g., of the carrier element.

According to an embodiment, at least an end portion of the electrical supply line includes a sleeve member and is electrically connected to the first and second flaps via the sleeve member.

In other words, the end portion of the electrical supply line may be reinforced by a sleeve member. The sleeve member may enclose a highly flexible end portion of, e.g., a braided wire or other elongate electrical conductor and may stiffen such end portion. The sleeve member may be a metallic sleeve. The sleeve member may be cylindrical and/or hollow. An inner diameter of the sleeve member may be slightly larger than an outer diameter of the elongate electrical conductor extending through the center of the sleeve member. The sleeve member may be crimped to the electrical conductor or electrically and mechanically connected to the electrical conductor in another manner. Due to the reinforcing sleeve member, the end portion of the electrical supply line may be easily handled during fabrication, disposed and aligned with the contact element and/or electrically connected to the flaps of the contact element.

According to a further specified embodiment, a bending radius of the bent portion of each flap corresponds, with a tolerance of ±30%, preferably a tolerance of ±20% or a tolerance of ±10%, to a quarter of an outer diameter of the sleeve.

Due to such specific curvature radius at the bent portion, the straight portion of the flap may generally extend at a suitable distance with regards to an abutment surface at the contact element, where the sleeve may be abutted upon arranging the supply line at the contact element. Particularly, the straight portion of the flap may extend at a distance to the abutment surface in the height direction, such distance corresponding to half of the diameter of the sleeve. At such height distance, the straight portion of the flap may form a suitable lateral abutment surface for aligning the end portion of the supply line and, additionally, may be easily accessible for welding the lateral edge of the straight portion of the flap to the sleeve of the supply line.

According to an embodiment, the contact element comprises a pair of first fastening flaps and a pair of second fastening flaps, each pair of fastening flaps comprising two flaps being arranged at opposite lateral sides of the electrical supply line with an end portion of the electrical supply line extending through a gap enclosed by opposing flaps of the respective pair of flaps.

In other words, a first pair of fastening flaps may be provided at a first rim of the contact element and a second pair of fastening flaps may be provided at an opposing second rim of the contact element. The flaps of each pair may be laterally spaced from each other such that the end portion of the supply line may be interposed between the opposing flaps. Accordingly, lateral edges of the opposing flaps may form opposing abutment surfaces between which the end portion of the supply line may be arranged and precisely held.

According to a further specified embodiment, a width of the gap between the opposing flaps corresponds to an outer diameter of the end portion of the electrical supply line.

Thus, the end portion of the supply line may be interposed between the opposing flaps and may laterally contact each of the flaps at their respective lateral edges. Preferably, the end portion of the supply line may then be attached, for example, welded, to each of the lateral edges of the opposing flaps. Thereby, the supply line may be precisely aligned with respect to the contact element and may be reliably held at the contact element.

According to an embodiment, the contact element including the flaps is integrally made from a single metal sheet by deep drawing, bending and/or punching.

Expressed differently, in order to prepare a contact element for the proposed electrode device, a metal sheet may be processed by deep drawing, bending and/or punching, thereby integrally forming not only the contact body with its contact surface but also integrally forming each of the flaps and, optionally, integrally forming the flanges at the rim of the contact element. Therein, the preferably cuboid contact body is typically formed by deep drawing the metal sheet. The flaps including their bent portions are typically formed by punching and bending portions of the metal sheet at its outer rim. By integrally forming the entire contact element from a single metal sheet, a fabrication procedure may be simplified while enabling contact elements being reliably and simply electrically connected to the electrical supply line.

It shall be noted that possible features and advantages of embodiments of the present invention are described herein with respect to various embodiments of the medical electrode device and with respect to various embodiments of the method for fabricating such electrode device. One skilled in the art will recognize that the features may be suitably transferred from one embodiment to another and features may be modified, adapted, combined and/or replaced, etc. in order to come to further embodiments of the present invention.

Additional features, aspects, objects, advantages, and possible applications of the present disclosure will become apparent from a study of the exemplary embodiments and examples described below, in combination with the Figures and the appended claims.

BRIEF DESCRIPTION OF THE DRAWINGS

In the following, advantageous embodiments of the present invention will be described with reference to the enclosed drawings. However, neither the drawings nor the description shall be interpreted as limiting the present invention.

The figures are only schematic and not to scale. Same reference signs refer to same or similar features.

DETAILED DESCRIPTION

Figure 1:
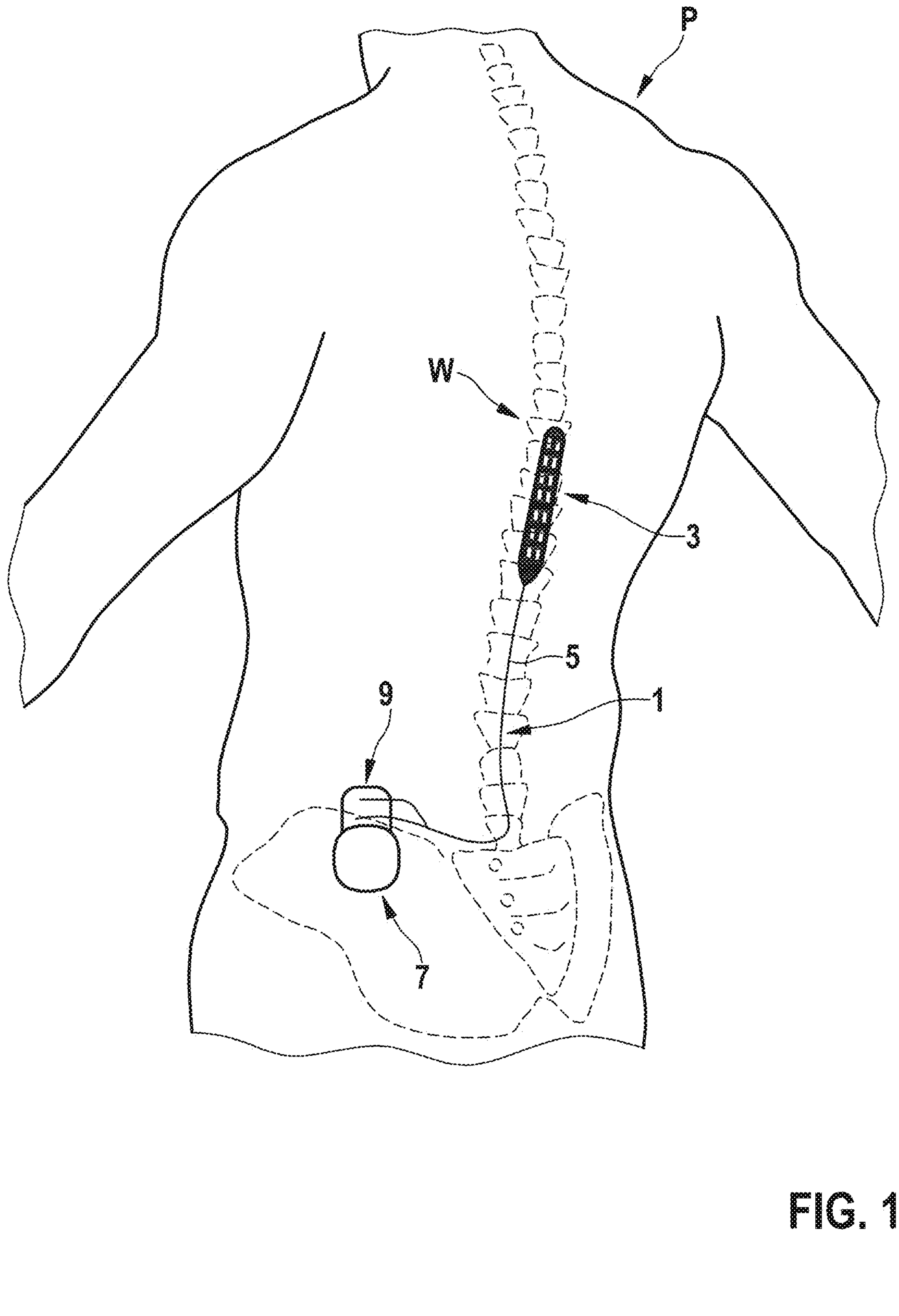
FIG. 1 shows a medical electrode device connected to a stimulation device in an implanted state in the area of the spine of a patient.
Figure 2:
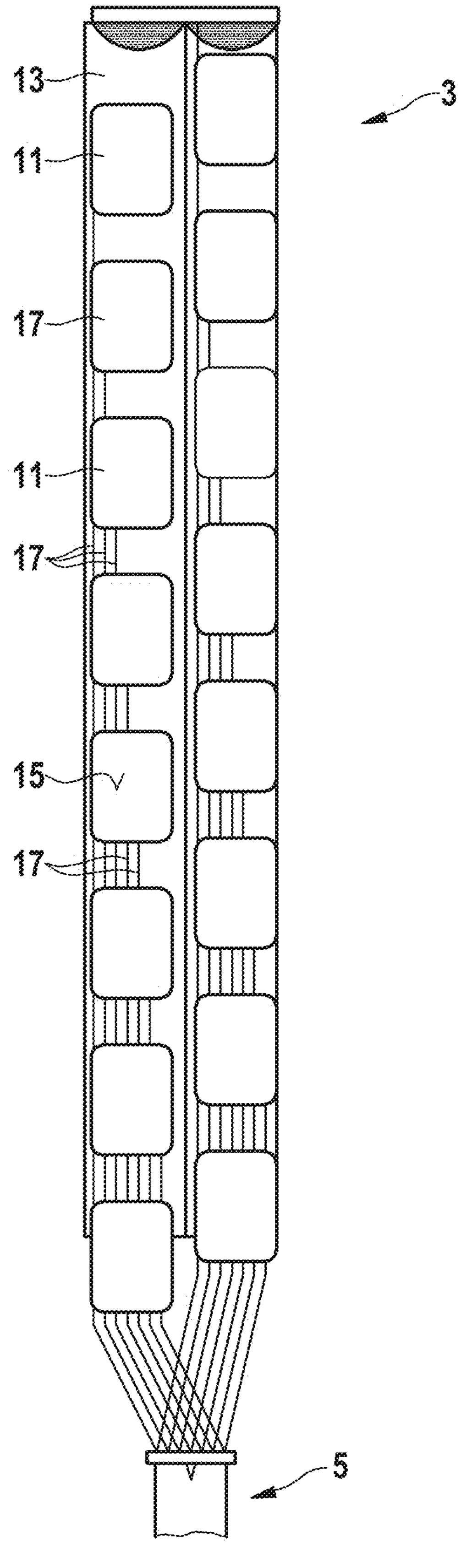
FIG. 2 shows a top view of an embodiment of a medical electrode device.
Figure 3:
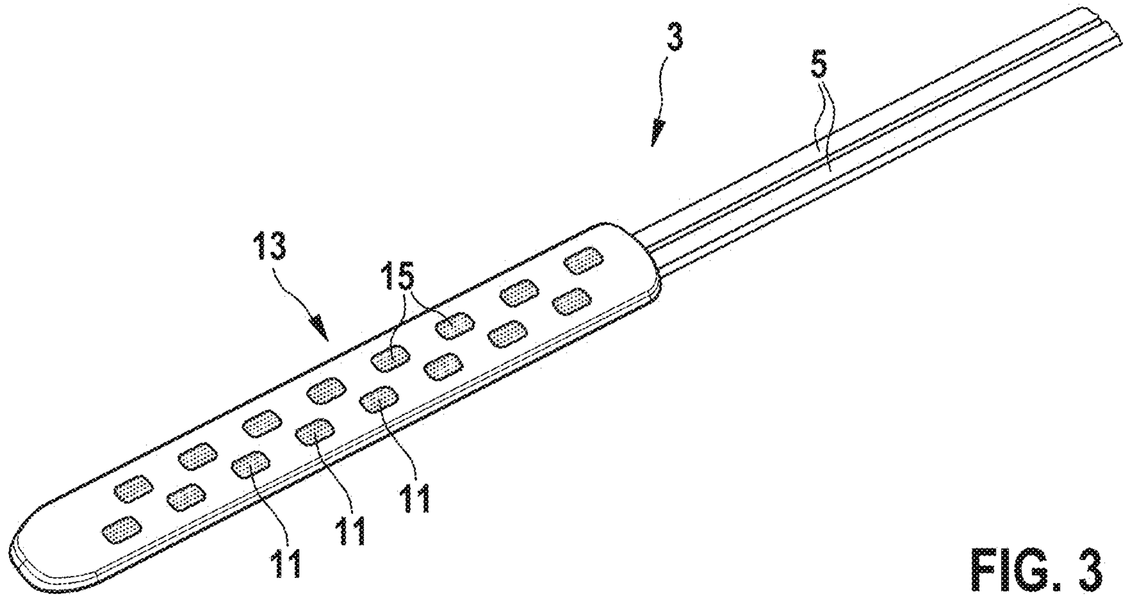
FIG. 3 shows a perspective view of an electrode device with contact elements arranged on a flattened end of the electrode device.

FIG. 1 shows a medical device 1 which may be applied for neurostimulation of nerves in a spinal column W of a patient P. FIGS. 2 and 3 show details of a medical electrode device 3 forming part of the medical device 1.

The medical electrode device 3 is formed as a so-called paddle electrode. The electrode device 3 is connected via a lead body 5 to a connector block 9 of a stimulation device 7. The stimulation device 7 may generate electrical stimulation currents to be delivered to the electrode device 3. The electrode device 3 comprises a plurality of contact elements 11 for injecting the electrical currents, e.g., in the region of the spinal column W.

While the lead body 5 may, for example, comprise a circular (isodiametric) cross-section or a flattened cross-section, the electrode device 3 is flattened as can be seen in FIGS. 2 and 3. The electrode device 3 carries the plurality of contact elements 11 in a flat, deformable carrier element 13 of electrically insulating material. The contact elements 11 may be evenly or unevenly spaced on the carrier element 13 in such a way that stimulation energy may be fed in a directed manner, for example, into the spinal cord R of the patient P.

As further illustrated in FIG. 2, each contact element 11 is connected to a supply line 17, wherein each contact element 11, for example, is connected to the stimulation device 7 via an associated, individual supply line 17 and thus may be supplied with stimulation energy via the stimulation device 7 to emit electrical signals. The supply lines 17 are jointly routed as a cable strand in the lead body 5 in an encapsulated manner to the stimulation device 7.

The contact elements 11 are arranged on the carrier element 13 and are exposed with a contact surface 15 facing outwards. The contact surface 15 may therefore come into contact with surrounding tissue when the electrode device 3 is implanted in the patient.

Figure 4:
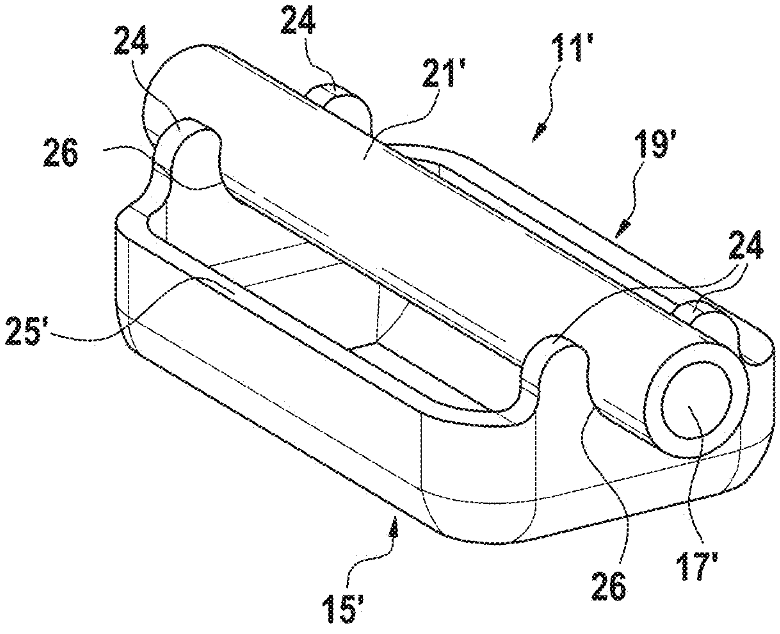
FIG. 4 shows a perspective view of an exemplary conventional contact element.

FIG. 4 shows the contact element 11' used in conventional electrode devices. The contact element 11' comprises a contact body 19' having a generally cuboid shape with rounded edges and corners. The contact body 19' forms a contact surface 15' at its front side. A supply line 17' stiffened at its end portion by a sleeve member 21' is connected mechanically and electrically to the contact element 11'. For such purpose, fastening sections 24 are provided at the contact elements 11'. In the example shown, four fastening sections 24 protrude from a rim 25' of the contact body 19'. Specifically, a pair of fastening sections 24 is provided at a distal end of the contact body 19' and another pair of fastening sections 24 is provided at a proximal end of the contact body 19'. Each pair of fastening sections 24 encloses the sleeve member 21' from opposing sides.

In such configuration, the supply line 17' may be precisely aligned and attached to the contact element 11'. However, for fixing the supply line 17' to the contact element 11', only very small fixation areas 26 of the contact element 11' may be welded to a lateral surface of the sleeve 21'. Generally, a width of such fixation areas 26 corresponds to a sheet thickness of a metal sheet forming the contact element 11'. Due to the miniaturization of the contact element 11', such sheet thickness may be generally less than 0.2 mm. Accordingly, attaching the contact element 11' to the supply line 17', for example, by welding, particularly by laser welding, may be complex and may require very precise alignment of, e.g., a welding laser beam. Furthermore, due to the small fixation areas 26, a mechanical loadability of the mechanical connection between the supply line 17' and the contact element 11' may be weak. Additionally, in cases where, for example, a welding laser beam is not perfectly aligned with the fixation areas 26 during a welding procedure, the laser beam may hit adjacent areas of the electrode device 3. Such adjacent areas may consist, for example, of heat sensitive material of, e.g., the carrier element. Accordingly, any slight misalignment of the welding laser beam may result in damages to the electrode device 3, for example, at its carrier element 13.

Figure 5:
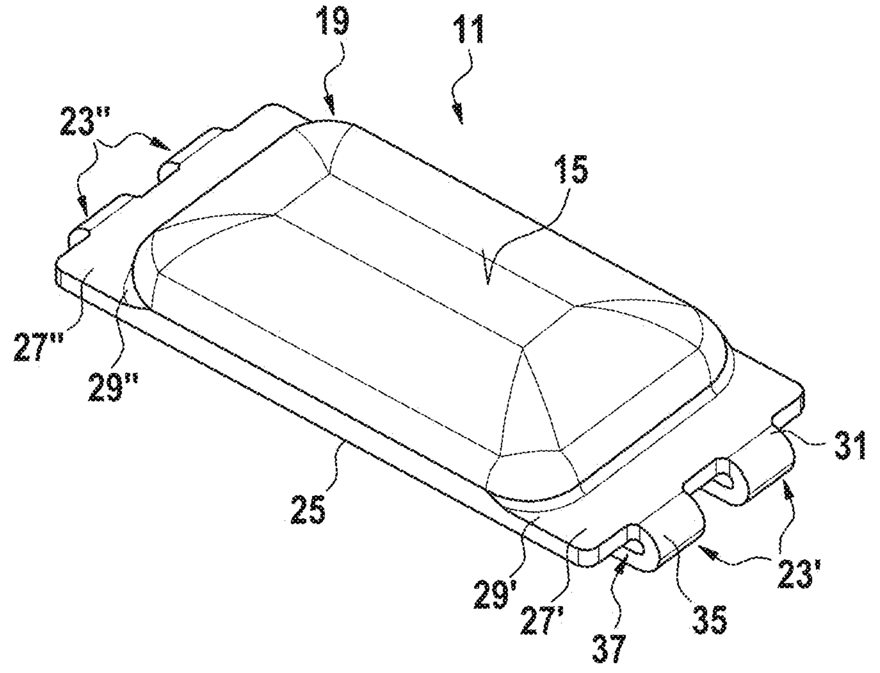
FIG. 5 shows a perspective top view of a contact element of an embodiment of the medical electrode device.
Figure 6:
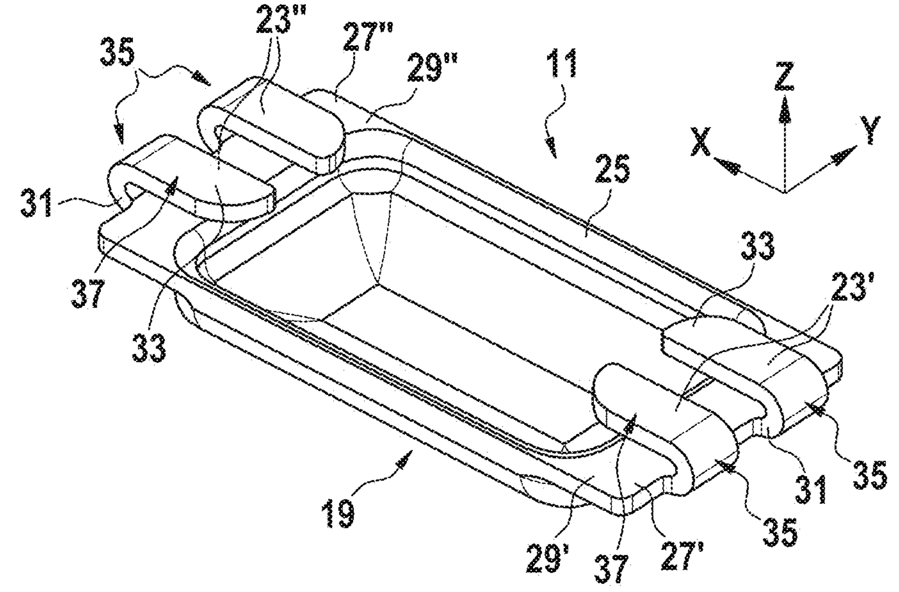
FIG. 6 shows a perspective bottom view of the contact element of FIG. 5.
Figure 7:
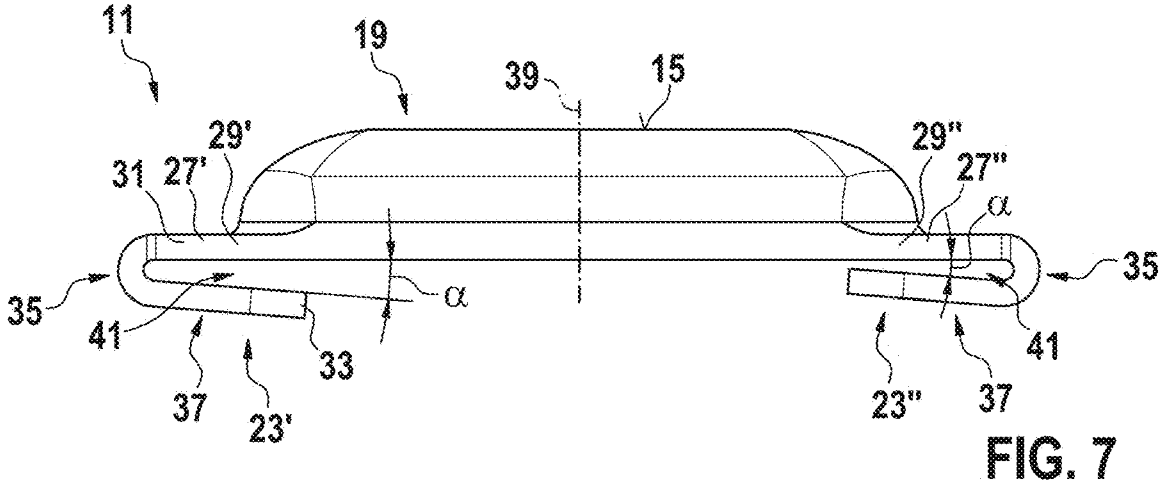
FIG. 7 shows a side view of the contact element of FIG. 5.

FIGS. 5-7 show a perspective top view, a perspective bottom view and a side view, respectively, of a contact element 11 for an electrode device 3 according to an embodiment of the present invention.

The contact element 11 comprises a substantially cuboid contact body 19 having rounded edges and corners. The contact body 19 comprises a contact surface 15 at its front side.

At a first rim portion 29', the contact body 19 comprises a first flange 27'. At a second rim portion 29", the contact body 19 comprises a second flange 27". The first and second rim portions 29', 29" are positioned at opposite ends of the contact element 11 with regard to its length direction X (indicated in FIG. 6). The flanges 27', 27" are generally planar, extend in a same plane and are substantially parallel to the contact surface 15 but spaced from this a contact surface 15 in the height direction Z.

The contact element 11 furthermore comprises first fastening flaps 23' and second fastening flaps 23". The first and second fastening flaps 23', 23" are arranged at a distance with respect to each other along the length direction X. Each of the first and second fastening flaps 23', 23" extends from a circumference formed by the rim 25 of the contact body 19. Particularly, the first and second fastening flaps 23', 23" extend from the first and second flanges 27', 27" provided at the first and second rim portions 29', 29". The first and second fastening flaps 23', 23" are formed integrally with the contact body 19. A first end 31 of each flap 23 integrally adjoins the rim 25 of the contact body 19 whereas a second end 33 of each flap is free, i.e., self-supporting and/or cantilever.

Each of the first and second flaps 23', 23" comprises a bent portion 35 and a straight portion 37. The bent portion 35 is at or close to the first end 31 of the flap 23 and therefore adjoins proximally to the circumference of the contact body 19. The straight portion 37 is at or close to the second end 33 of the flap 23 and therefore extends distal to the circumference of the contact body 19. Particularly, the first flaps 23' extend from a first end edge of the contact body 19 formed by the first flange 27' at the first rim portion 29' and the second flaps 23" extend from a second end edge opposite to the first end edge, this second end edge being formed by the second flange 27". Therein, each of the first and second flaps 23', 23" are directed with their second ends 33 towards a center 39 (see FIG. 7) of the contact body 19.

As visualized particularly in FIG. 7, the bent portions 35 of the flaps 23 are bent such that the adjoining flat portions 37 extend, with a certain tolerance, in parallel to the flanges 27 of the contact body 19.

Therein, in the example shown in the figures, the bent portions 35 comprise a curvature radius being substantially larger than 0, such that the adjoining flat portion 37 is arranged spaced apart from the contact body 19 and its flange 27. Accordingly, a gap 41 is provided between the flat portion 37 of the flap 23 and the flange 27 of the contact body 19. Such gap 41 may serve for thermal isolation between the flat portion 37 of the flap 23 and the rest of the contact body 19, for example, during a welding procedure for welding the flap 23 to the supply line 17.

In an alternative embodiment (not shown), the bent portion 35 may be provided with a curvature radius being substantially 0, such that the adjoining flat portion 37 directly abuts to the contact body 19 and its flange 27. In such embodiment, a material thickness of a welding area formed by the flap 23 is effectively doubled.

Furthermore, an orientation α (see FIG. 7) of the straight portion 37 of the flap 23 with regards to the associated flange 27 may vary as a result of fabrication tolerances. However, such variations generally do not affect a functionality of the flap 23. In fact, such orientation may be specifically varied or set, thereby varying, for example, the dimension of the gap 41 in an intended manner.

FIGS. 8-11 visualize various examples of a contact element 11 being connected to a supply line 17.

Figure 8:
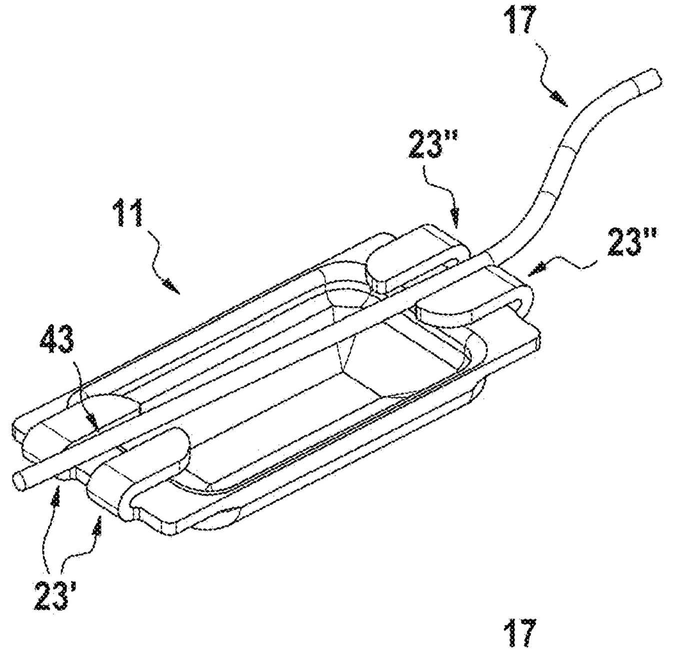
FIGS. 8-11 show perspective bottom views of contact elements of various embodiments of the medical electrode device.
Figure 10:
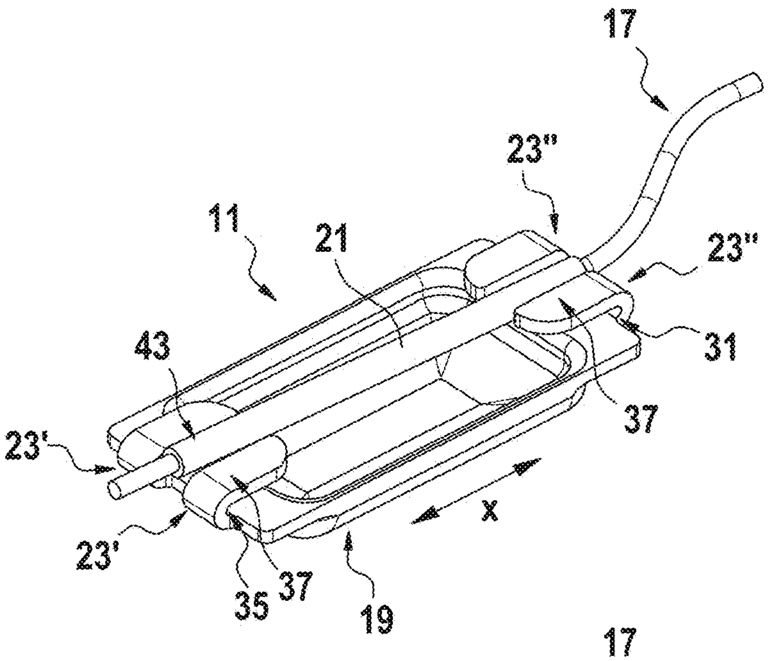

Therein, in the examples shown in FIGS. 8 and 10, the contact element 11 comprises a pair of first fastening flaps 23' and a pair of second fastening flaps 23" provided at opposite ends of the contact element 11. Each pair of fastening flaps 23', 23" comprises two flaps arranged at opposite lateral sides of the electrical supply line 17. Accordingly, the supply line 17 extends through a gap 43 enclosed by the opposing flaps 23 of the respective pair of flaps. A width of such gap 43 corresponds to an outer diameter of the end portion of the electrical supply line 17.

Figure 9:
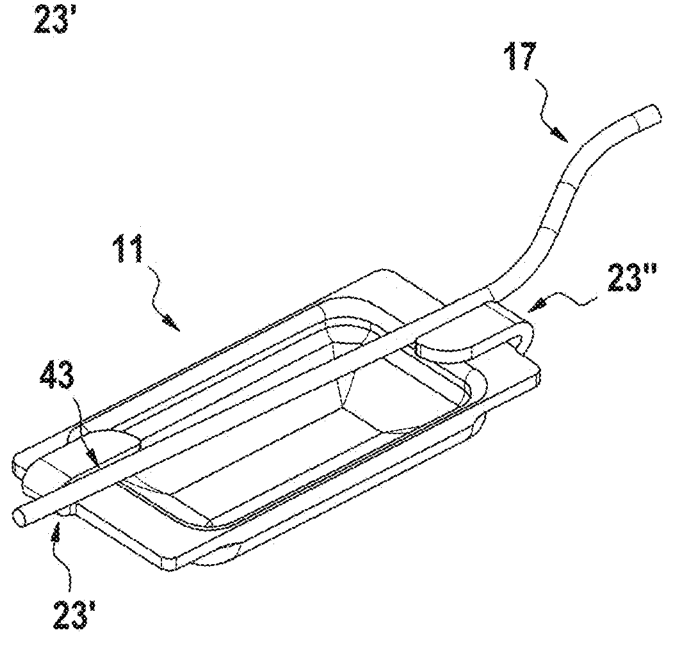
Figure 11:
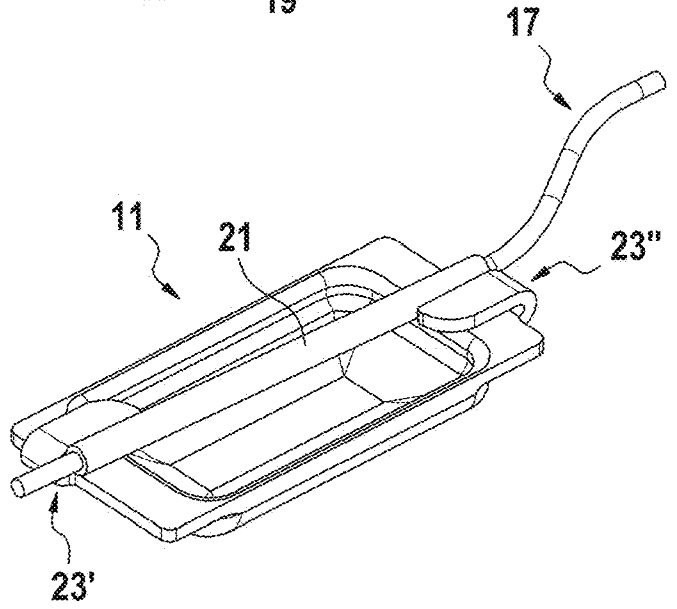

In the examples shown in FIGS. 9 and 11, only one first fastening flap 23' and only one second fastening flap 23" is provided at opposite ends of the contact element 11. Therein, the first and second fastening flaps 23', 23" are arranged at opposite lateral sides of the end portion of the supply line 17.

In the examples shown in FIGS. 10 and 11, the end portion of the supply line 17 comprises a sleeve member 21. Such sleeve member 21 may, for example, stiffen a highly bendable braided wire extending through a center of such sleeve member 21. The supply line 17 is then connected to the first and second flaps 23', 23" via the sleeve member 21.

Figure 12:
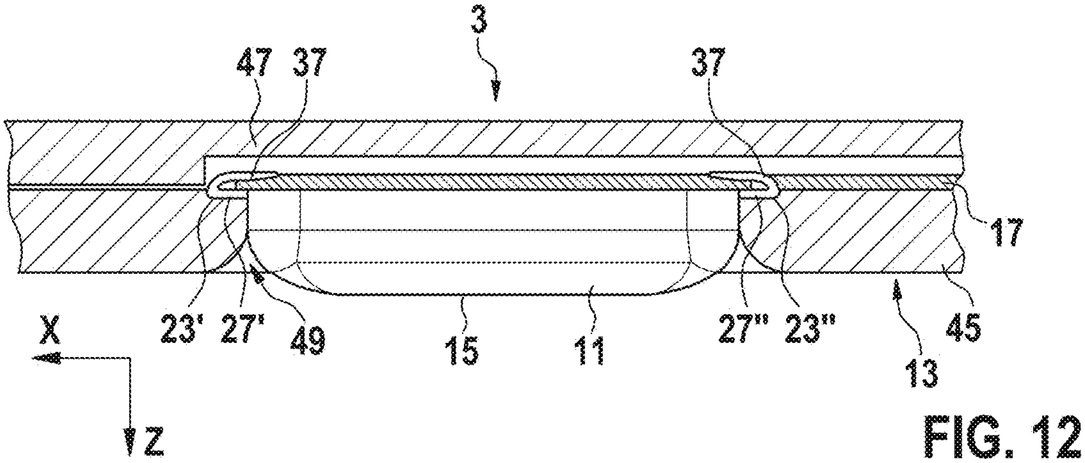
FIG. 12 shows a cross-sectional view of a contact element included in an embodiment of the medical electrode device.

FIG. 12 schematically shows a longitudinal cross-section through an exemplary medical electrode device 3. The contact element 11 slightly protrudes with its contact surface 15 from a surface of the carrier element 13. In this example, the carrier element 13 comprises a front side part 45 and a rear side part 47.

Upon fabricating the electrode device 3, the contact element 11 is arranged within a cavity 49 comprised in the front side part 45 of the carrier element 13. Then, the supply line 17 is arranged such that its end portion is disposed on the first and second flanges 27', 27" of the contact element 11. Therein, at least one lateral surface or opposing lateral surfaces contact one or two opposing first and second fastening flaps 23', 23", respectively. Upon the end portion of the supply line 17 being correctly aligned with regards to the contact element 11, the straight portions 37 of the first and second fastening flaps 23', 23" are connected to the supply line 17 by laser welding along a lateral contact surface extending along a side edge of the straight portion 37 of each of the respective flaps 23. Finally, a rear side 47 of the carrier element 13 may be closed by the rear side part 47.

Embodiments of the medical electrode device 3 proposed herein may offer, inter-alia, a variety of advantages as follows:

- The contact element design described and the lead connection may allow tolerance compensation after assembly, which may be very large depending on the length of the retaining flaps and the crimp sleeves.
- The design described takes into account that the electrode contact may be produced by means of deep-drawing stamping and bending processes.
- Without applying a filler material, it is possible to locally double the wall thickness of the exit material if the flaps are folded over completely without a gap (bending radius 0 mm) and pressed onto the contact surface, which leads to an increase in the available material volume and thus better weldability.
- Thanks to the design with folded-down retaining flaps, welding of the supply line (if necessary with additional component, e.g., crimp sleeve) can take place far away from neighboring components (insulation material/carrier material/paddle). Thermal damage to the neighboring components can thus be avoided.
- If the flaps are folded over with a bending radius >0 mm, an air gap is created between the bending flap and the base material. This can also prevent thermal damage to the base material located under the welding position, since the lower layer of the electrode contact can serve as a "laser beam trap".
- In principle, the design makes it possible to process different diameters of the supply line (if necessary with additional components) by varying the width of the flap breakout and variable design of the 180° bend (bending radius may be adapted to the geometry of the feed line/crimp sleeve as required).
- The design described may ensure parallel guidance of the lead in relation to the electrode contact, since it can always rest on the electrode contact over as large an area as possible and is only fixed laterally by the retaining flaps.
- The design of the folded-down side flaps (retaining flaps) may also reduce the influence of employees during assembly and welding, as it enables a lower requirement for manual positioning accuracy.
- The design is suitable for connecting both rigid leads and flexible leads (with additional components such as crimp sleeves, if necessary).
- The dimensions of the side plates or flanges may be varied as required depending on the design of the electrode contact.
- A process for manufacturing an electrode device of the kind described herein may be easily automatable.

Finally, it should be noted that the term "comprising" does not exclude other elements or steps and the "a" or "an" does not exclude a plurality. Also elements described in association with different embodiments may be combined. It should also be noted that reference signs in the claims should not be construed as limiting the scope of the claims.

It will be apparent to those skilled in the art that numerous modifications and variations of the described examples and embodiments are possible in light of the above teachings of the disclosure. The disclosed examples and embodiments are presented for purposes of illustration only. Other alternate embodiments may include some or all of the features disclosed herein. Therefore, it is the intent to cover all such modifications and alternate embodiments as may come within the true scope of this invention, which is to be given the full breadth thereof. Additionally, the disclosure of a range of values is a disclosure of every numerical value within that range, including the end points.

LIST OF REFERENCE NUMERALS

1 medical device
3 medical electrode device
5 lead body
7 stimulation device
9 connector block
11 contact element
13 carrier element
15 contact surface
17 supply line
19 contact body
21 sleeve member
23 fastening flap
24 fastening section
25 rim
26 fixation area
27 flange
29 rim portion
31 first end of flap
33 second end of flap
35 bent portion
37 straight portion
39 center
41 gap between straight portion of flap and flange
43 gap between opposing flanges of a flange pair
45 front side part of carrier element
47 rear side part of carrier element
49 cavity

The invention claimed is:

1. A medical electrode device for implantation into a patient, comprising:

a carrier element being formed with an electrically insulating material, at least one contact element arranged at the carrier element and comprising a contact body including a contact surface for contacting tissue of the patient in an implanted state of the medical electrode device, and at least one electrical supply line, an end portion of the electrical supply line being electrically connected to the contact element, wherein the contact element comprises at least one first fastening flap and at least one second fastening flap, the first fastening flap and the second fastening flap being arranged at a distance with respect to each other along a length direction, and the electrical supply line being connected to the contact element at the first fastening flap and the second fastening flap such that the electrical supply line is arranged at a distance with respect to the contact surface along a height direction oriented perpendicularly to the length direction, wherein each of the first and second flaps extends from a circumference of the contact body with a first end of each flap being integral with the contact body and a second end of each flap being free, wherein each of the first and second flaps comprises a bent portion proximal to the circumference of the contact body and a straight portion distal to the circumference of the contact body, and wherein each of the first and second flaps is physically connected to the electrical supply line with a lateral contact surface extending along a side edge of the straight portion of the respective flap.

2. The medical electrode device according to claim 1, wherein the first flap extends from a first end edge of the contact body and the second flap extends from a second end edge opposite to the first end edge of the contact body, and wherein each of the first and second flaps is directed with its second end towards a center of the contact body.

3. The medical electrode device according to claim 1, wherein a lateral rim of the respective flap extending along a side edge of the straight portion of the flap is welded to a circumferential surface of the end portion of the electrical supply line.

4. The medical electrode device according to claim 1, wherein the contact body comprises a first flange extending along a first rim portion of the contact body and a second flange extending along a second rim portion of the contact body opposite to the first rim portion, wherein the first flap extends from the first flange and the second flap extends from the second flange.

5. The medical electrode device according to claim 4, wherein the straight portions of each of the first and second flaps extend, with a tolerance of ±30°, in parallel to the flange from which the respective flap extends.

6. The medical electrode device according to claim 4, wherein the electrical supply line abuts with a portion of its lateral surface to each of the first and second flanges.

7. The medical electrode device according to claim 1, wherein the bent portion of the flap is bent such that the straight portion of the flap directly abuts to a portion of the contact body.

8. The medical electrode device according to claim 1, wherein the bent portion of the flap is bent such that the straight portion of the flap is spaced from a portion of the contact body via an intermediate gap.

9. The medical electrode device according to claim 1, wherein at least the end portion of the electrical supply line includes a sleeve member and is electrically connected to the first and second flaps via the sleeve member.

10. The medical electrode device according to claim 9, wherein a bending radius of the bent portion of each flap corresponds, with a tolerance of ±30%, to a quarter of an outer diameter of the sleeve.

11. The medical electrode device according to claim 1, wherein the contact element comprises a pair of first fastening flaps and a pair of second fastening flaps, each pair of fastening flaps comprising two flaps being arranged at opposite lateral sides of the electrical supply line with the end portion of the electrical supply line extending through a gap enclosed by opposing flaps of the respective pair of flaps.

12. The medical electrode device according to claim 11, wherein a width of the gap corresponds to an outer diameter of the end portion of the electrical supply line.

13. The medical electrode device according to claim 1, wherein the contact element including the flaps is integrally made from a single metal sheet by deep drawing, bending and/or punching.

14. A method for fabricating a medical electrode device for implantation into a patient, the method comprising:

providing a carrier element from an electrically insulating material, providing at least one contact element, providing at least one electrical supply line, arranging the contact element at least partially in the electrically insulating material of the carrier element such that the contact element-comprises a contact surface for coupling to tissue of the patient in an implanted state of the medical electrode device, and wherein the contact element comprises at least one first fastening flap and at least one second fastening flap, the first fastening flap and the second fastening flap being arranged at a distance with respect to each other along a length direction, and the electrical supply line being connected to the contact element at the first fastening flap and the second fastening flap such that the electrical supply line is arranged at a distance with respect to the contact surface along a height direction oriented perpendicularly to the length direction, wherein each of the first and second flaps extends from a circumference of the contact body with a first end of each flap being integral with the contact body and a second end of each flap being free, wherein each of the first and second flaps comprises a bent portion proximal to a circumference of the contact body and a straight portion distal to the circumference of the contact body, and wherein the method comprises physically connecting each of the first and second flaps to the electrical supply line with a lateral contact surface extending along a side edge of the straight portion of the respective flap.

15. The method according to claim 14, wherein the first and second flaps are connected to the electrical supply line by welding a lateral rim of the flap extending along the side edge of the straight portion of the respective flap to a circumferential surface of an end portion of the electrical line.

* * * * *